United States Patent
Nordquist et al.

(10) Patent No.: US 6,610,628 B2
(45) Date of Patent: *Aug. 26, 2003

(54) POLYMER NETWORK/CARBON LAYER ON MONOLITH SUPPORT AND MONOLITH CATALYTIC REACTOR

(75) Inventors: Andrew Francis Nordquist, Whitehall, PA (US); Frederick Carl Wilhelm, Zionsville, PA (US); Francis Joseph Waller, Allentown, PA (US); Reinaldo Mario Machado, Allentown, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 16 days.

This patent is subject to a terminal disclaimer.

(21) Appl. No.: 09/867,959

(22) Filed: May 30, 2001

(65) Prior Publication Data

US 2003/0027718 A1 Feb. 6, 2003

Related U.S. Application Data

(63) Continuation-in-part of application No. 08/839,699, filed on Apr. 20, 2001, now abandoned.

(51) Int. Cl.[7] .......................... B01J 31/06; B01J 21/18; B01J 23/38; B01J 23/70
(52) U.S. Cl. .................. 502/159; 502/180; 502/182; 502/185; 502/305; 502/339; 502/345; 502/527.24
(58) Field of Search .................. 502/159, 180, 502/182, 185, 339, 305, 345, 527.24

(56) References Cited

U.S. PATENT DOCUMENTS 4,532,228 A * 7/1985 Golino et al. ............ 423/213.5
4,743,577 A   5/1988 Schroeder et al. .......... 502/326
5,250,490 A   10/1993 Ritscher et al. ............ 502/313
5,658,372 A * 8/1997 Gadkaree .................. 95/116
6,005,143 A   12/1999 Machado et al. ........... 564/423

FOREIGN PATENT DOCUMENTS

EP    0233642    8/1987

OTHER PUBLICATIONS

Hatziantoniou, et al. "The Segmented Two–Phase Flow Monolithic Catalyst Reactor. An Alternative for Liquid–Phase Hydrogenations", Ind. Eng. Chem. Fundam., vol. 23, No. 1, 82–88 (1984) No Month.

Hatziantoniou, et al. "Mass Transfer and Selectivity in Liquid–Phase Hydrogenation of Nitro Compounds in a Monolithic Catalyst Reactor with Segmented Gas–Liquid Flow", Ind. Eng. Chem. Process Des. Dev., vol. No. 4, 964–970 (1986), No Month.

Report by Delf University, Elsevier Science B.V., Preparation of Catalysts VII, pp. 175–183 (1998), No Month.

* cited by examiner

Primary Examiner—Elizabeth D. Wood
(74) Attorney, Agent, or Firm—Keith D. Gourley

(57) ABSTRACT

The present invention relates to an improved monolith catalytic reactor and a monolith support. The improvement in the support resides in a polymer network/carbon coating applied to the surface of a porous substrate and a catalytic metal, preferably a transition metal catalyst applied to the surface of the polymer network/carbon coating. The monolith support has from 100 to 800 cells per square inch and a polymer network/carbon coating with surface area of from 0.1 to 15 $m^2$/gram as measured by adsorption of $N_2$ or Kr using the BET method.

5 Claims, No Drawings

POLYMER NETWORK/CARBON LAYER ON MONOLITH SUPPORT AND MONOLITH CATALYTIC REACTOR

CROSS-REFERENCE TO RELATED APPLICATIONS

This application is a continuation-in-part of U.S. Ser. No. 09/839,699 filed Apr. 20, 2001, now abandoned, and entitled Hydrogenation With Monolith Reactor Under Conditions Of Immiscible Liquid Phases, the specification and claims which are incorporated by reference herein.

STATEMENT REGARDING FEDERALLY SPONSORED RESEARCH OR DEVELOPMENT

The subject matter presented in this patent application was funded in part by the United States Department of Energy (DOE) under Cooperative Agreement No. DE-FC02-00CH11018. The DOE may possess certain rights underthe claims appended hereto.

BACKGROUND OF THE INVENTION

Industrial hydrogenation reactions are often performed by using finely divided powdered slurry catalysts in stirred-tank and reactors. These slurry phase reaction systems are inherently problematic in chemical process safety, operability and productivity. The finely divided, powdered catalysts are often pyrophoric and require extensive operator handling during reactor charging and filtration. By the nature of their heat cycles for start-up and shut-down, slurry systems promote co-product formation which can shorten catalyst life and lower yield to the desired product.

An option to the use of finely divided powder catalysts in stirred reactors has been the use of pelleted catalysts in fixed bed reactors. While this reactor technology does eliminate much of the handling and waste problems, a number of engineering challenges have not permitted the application of fixed bed reactor technology to the hydrogenation of many organic compounds. Controlling the overall temperature rise and temperature gradients in the reaction process has been one problem. A second problem is that in fixed bed packed reactors there is a significant pressure drop due to the high flow rates required for hydrogenation. A third problem is that liquid-gas distribution is problematic thus often leading to poor conversion and localized concentration gradients. A fourth problem is that the product water phase in a two liquid phase system tends to block access of the reactant to the active catalyst sites and thereby decrease the reaction rate or, in the alternative, result in inconsistent reaction rates.

Monolith catalytic reactors are an alternative to fixed bed reactors and have a number of advantages over conventional fixed bed reactors. These reactors have low pressure drop which allow them to be operated at higher gas and liquid velocities. These higher velocities of gas and liquids promote high mass transfer and mixing and the parallel channel design of a monolith inhibits the coalescence of the gas in the liquid phase.

Monolith catalytic reactor development has been an ongoing process in an effort to enhance catalytic activity and catalyst life. Exposure of the catalytic metal in the monolith catalytic reactor to the reactants is necessary to effect good reaction rates. However, efforts to enhance exposure of the catalytic metal often are at odds with enhancing adhesion of the metal to the monolith substrate. Embedding the catalytic metal in a coating applied to the surface of the monolith may result in greater adhesion of the catalytic metal but also reduces catalytic activity.

The following articles and patents are representative of catalytic processes employing monolith catalysts and processes in chemical reactions including the hydrogenation of nitroaromatics and other organic compounds.

Hatziantoniou, et al. in "The Segmented Two-Phase Flow Monolithic Catalyst Reactor. An Alternative for Liquid-Phase Hydrogenations", Ind. Eng. Chem. Fundam., Vol. 23, No.1, 82–88 (1984) discloses the liquid phase hydrogenation of nitrobenzoic acid (NBA) to aminobenzoic acid (ABA) in the presence of a solid palladium monolithic catalyst. The monolithic catalyst consisted of a number of parallel plates separated from each other by corrugated planes forming a system of parallel channels having a cross sectional area of 1 $mm^2$ per channel. The composition of the monolith comprised a mixture of glass, silica, alumina, and minor amounts of other oxides reinforced by asbestos fibers with palladium metal incorporated into the monolith in an amount of 2.5% palladium by weight. The reactor system was operated as a simulated, isothermal batch process. Feed concentrations between 50 and 100 moles/$m^3$ were cycled through the reactor with less than 10% conversion per pass until the final conversion was between 50% and 98%.

Hatziantoniou, et al. in "Mass Transfer and Selectivity in Liquid-Phase Hydrogenation of Nitro Compounds in a Monolithic Catalyst Reactor with Segmented Gas-Liquid Flow", Ind. Eng. Chem. Process Des. Dev., Vol. 25, No.4, 964–970 (1986) discloses the isothermal hydrogenation of nitrobenzene and m-nitrotoluene dissolved in ethanol using a monolithic support impregnated with palladium. The authors report that the activity of the catalyst is high and therefore mass-transfer is rate determining. Hydrogenation was carried out at 590 and 980 kPa at temperatures of 73 and 103° C. Again, less than 10% conversion per pass was achieved. Ethanol was used as a cosolvent to maintain one homogeneous phase.

U.S. Pat. No. 6,005,143 discloses a process for the adiabatic hydrogenation of dinitrotoluene in a monolith catalyst employing nickel and palladium as the catalytic metals. A single phase dinitrotoluene/water mixture in the absence of solvent is cycled through the monolith catalyst under plug flow conditions for producing toluenediamine.

U.S. Pat. No. 4,743,577 discloses metallic catalysts which are extended as thin surface layers upon a porous, sintered metal substrate for use in hydrogenation and decarbonylation reactions. In forming a monolith, a first active catalytic material, such as palladium, is extended as a thin metallic layer upon a surface of a second metal present in the form of porous, sintered substrate. The resulting catalyst is used for hydrogenation, deoxygenation and other chemical reactions. The monolithic metal catalyst incorporates catalytic materials, such as, palladium, nickel and rhodium, as well as platinum, copper, ruthenium, cobalt and mixtures. Support metals include titanium, zirconium, tungsten, chromium, nickel and alloys.

U.S. Pat. No. 5,250,490 discloses a catalyst made by an electrolysis process for use in a variety of chemical reactions such as hydrogenation, deamination, amination and so forth. The catalyst is comprised of a noble metal deposited, or fixed in place, on a base metal, the base metal being in form of sheets, wire gauze, spiral windings and so forth. The preferred base metal is steel which has a low surface area, e.g., less than 1 square meter per gram of material. Catalytic metals which can be used to form the catalysts include platinum, rhodium, ruthenium, palladium, iridium and the like.

EPO 0 233 642 discloses a process for the hydrogenation of organic compounds in the presence of a monolithsupported hydrogenation catalyst. A catalytic metal, e.g., Pd, Pt, Ni, or Cu is deposited or impregnated on or in the monolith support. A variety of organic compounds are suggested as being suited for use and these include olefins, nitroaromatics and fatty oils.

There is a report by Delft University, in Elsevier Science B.V., Preparation of Catalysts VII, p. 175–183 (1998) that discloses a carbon coated ceramic monolith where the carbon serves as a support for catalytic metals. Ceramic monolith substrates were dipped in furfuryl alcohol based polymer forming solutions and allowed to polymerize. After solidification the polymers were carbonized in flowing argon to temperatures of 550° C. followed by partial oxidation in 10% $O_2$ in argon at 350° C. The carbon coated monolith substrate typically had a surface area of 40–70 $m^2$/gram.

BRIEF SUMMARY OF THE INVENTION

The present invention relates to an improved process for the hydrogenation of an immiscible mixture of an organic reactant in water. The two phase immiscible mixture can result from the generation of water during the hydrogenation reaction itself or, by the addition of water to the reactant prior to contact with the catalyst or to the reactor. The improvement resides in effecting the hydrogenation of a two phase immiscible mixture of organic reactant in water in a monolith catalytic reactor comprised of a monolith support and a catalytic metal and having from 100 to 800 cells per square inch (cpi). This is accomplished by passing a two phase immiscible mixture of organic reactant in water through the reactor at a superficial velocity of from 0.1 to 2 m/second in the absence of a cosolvent for the two phase immiscible mixture.

The invention also relates to an improved monolith support comprised of a substrate having a polymer network/carbon coating applied to its surface, and, also, to an improved monolith catalytic reactor comprised of the monolith support and a catalytic metal, preferably a transition metal catalyst.

Several advantages are achievable in the process through the use of a monolith catalytic reactor and these include:

an ability to effect liquid phase hydrogenation of organic compounds as an immiscible phase in water and in the absence of a cosolvent;

an ability to obtain high throughput of product through the catalytic unit even though the reaction rate may be less than that using a cosolvent;

an ability to generate a monolith support suited for impregnation with a variety of catalytic metals and thereby forming a monolith catalytic reactor having excellent activity;

an ability to effect hydrogenation reactions at a consistent reaction rate; and, an ability to hydrogenate organic reactants under liquid phase conditions that permit ease of separation of reactants and byproduct.

DETAILED DESCRIPTION OF THE INVENTION

The present invention relates to an improved process for the hydrogenation of an immiscible mixture (two phases) of an organic reactant in water. The immiscible mixture can result from the generation of water during the hydrogenation reaction or, if desired, by the addition of water to the reactant prior to or during the hydrogenation reaction.

There are numerous categories of organic compounds having functional groups that may be hydrogenated as a two phase mixture. The functional groups include nitro, anhydride, and the reaction product of a ketone or aldehyde and ammonia, aromatic amine, primary or secondary amine. The following are hydrogenation reactions involving these functional groups that co-produce water and can be hydrogenated in a monolith catalytic reactor.

Nitro Group Reduction $$RNO_2 + 3H_2 \rightarrow RNH_2 + 2H_2O$$

where R is aromatic. Many nitro aromatics are capable of undergoing the hydrogenation reaction described by the process of this invention. Typical nitroaromatics are nitrobenzene, nitrotoluenes, nitroxylenes, nitroanisoles and halogenated nitroaromatics where the halogen is Cl, Br, I, or F.

Anhydride Reduction to Lactone or Ether

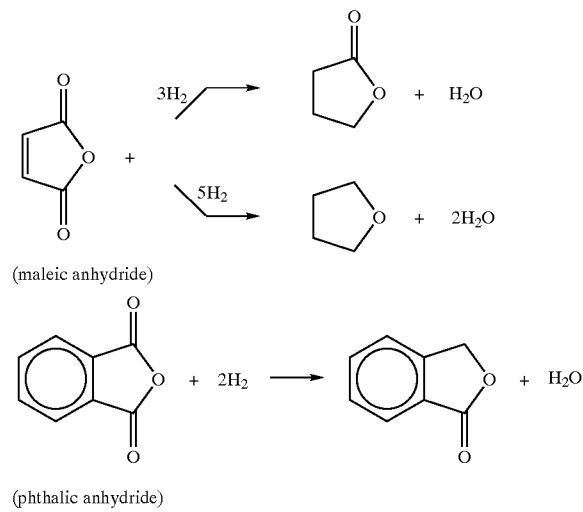

(maleic anhydride)

(phthalic anhydride)

Anhydrides such as maleic anhydride and phthalic anhydride are first hydrogenated to γ-butyrolactone and phthalide respectively. The γ-butyrolactone can be further reduced to tetrahydrofuran.

Reductive Alkylation or Reductive Amination

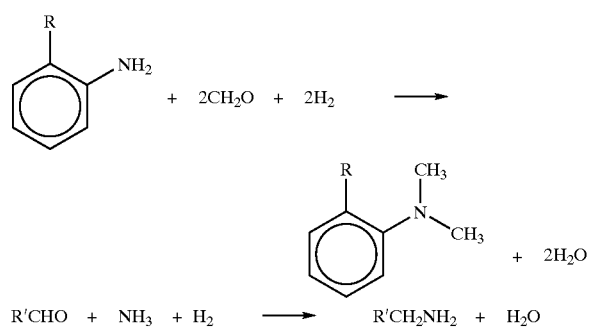

When an aldehyde or a ketone is treated with ammonia or a primary or secondary amine in the presence of hydrogen and a hydrogenation catalyst, reductive alkylation of ammonia or the amine or reductive amination of the carbonyl compound takes place. R and R' can be aromatic or aliphatic. Examples of aldehydes and ketones useful in the hydrogenation reactions include formaldehyde, cyclohexanone and methyl isopropyl ketone. Reaction products resulting from the reaction of these aldehydes and ketones with primary and secondary amines include N-methylcyclohexylamine, N-methyldicyclohexylamine, N,N-dimethylcyclohexylamine, N-ethylcyclohexylamine, dicyclohexylamine, N,N-diethylcyclohexylamine, N,N,N'-trimethylaminoethylethanolamine, N-ethyl-1,2-dimethylpropylamine and N,N,N',N'-tetramethylpropanediamine.

By immiscibility of the reaction system leading to the presence of two phases, it is meant that two liquid phases are present at the operating temperature. The solubility of the organic reactant in water is not only a function of temperature but also a function of the solubility of the reaction product(s) with the organic reactant and with water. In some hydrogenation reaction systems, e.g., the hydrogenation of dinitrotoluene, the dinitrotoluene reactant, the toluenediamine reaction product and water produce essentially one liquid phase at stoichiometric reaction conditions of 60% toluenediamine, 39% water and 1% dinitrotoluene. In the hydrogenation of nitrobenzene, however, the reaction products of nitrobenzene, aniline and water, on the other hand, remain as a two phase system throughout the hydrogenation process. The following solubility data is for aniline in water and nitrobenzene in water at different temperatures.

|  | Temperature | | |
| --- | --- | --- | --- |
|  | 20° C. | 80° C. | 90° C. |
| Aniline | 3.4 g per 100 g $H_2O$ | — | 6.4 g per 100 g $H_2O$ |
| Nitrobenzene | 0.19 g 100 g $H_2O$ | 0.8 g per 100 g $H_2O$ | — |

Monolith catalysts, or sometimes referred herein as monolith catalytic reactors, employed herein consist of a monolith support which is based upon an inorganic porous substrate, a metallic substrate or a carbon based substrate. Sometimes the surface of the monolith substrate may be modified, as for example, with a coating derived from a carbon or a heat treated network polymer and thereby form a monolith support having a modified substrate. Often the monolith catalytic reactors are based upon a honeycomb of long narrow capillary channels, circular, square or rectangular, whereby gas and liquid are co-currently passed through the channels under a laminar flow regime. The flow of gas and liquid in these confined channels and under these conditions promotes "Taylor" flow with bubbles of gas, typically $H_2$, squeezing past the liquid. This capillary action promotes very high initial gas-liquid and liquid-solid mass transfer.

The pressure drop within an effective monolith catalytic reactor can range from 2 kPa/m to 200 kPa/m for combined gas/liquid superficial velocities between 0.1 to 2 meters/second for 50% gas holdup in a monolith catalytic reactor having 400 cpi (cells per square inch). Typical dimensions for a honeycomb monolith catalytic reactor cell wall spacing range from 1 to 10 mm between the plates. Alternatively, the monolith catalytic reactor may have from 100 to 800, preferably 200 to 600 cpi. Channels or cells may be square, hexagonal, circular, elliptical, etc. in shape. (For purposes of convenience, it is assumed a monolith catalytic reactor comprised of the monolith support, whether a substrate or a network polymer containing including the catalytic metal, has the same cpi as the monolith substrate itself.)

Catalytic metals suited for the hydrogenation of water immiscible organics are impregnated or directly coated onto the monolithic substrate, a modified substrate or a washcoat which has been deposited onto the monolith. The catalytic metals include those Group VIb, Group VIIb, Group VIII, and Group Ib metals of the periodic table and conventionally used in hydrogenation reactions. Examples of catalytic metal components include rhodium, cobalt, Raney or sponge nickel, palladium, platinum, copper, ruthenium, rhenium and so forth. Often a mixture of metals are employed, one example being a mixture of palladium and nickel. For a monolith catalytic reactor where the monolith support is impregnated with a washcoat, the composition of catalytic metals is typically identified as a weight percent within the washcoat itself. The washcoat may be applied in an amount of from 1 to 50% of the monolith total weight. Typical catalyst metal loadings, then, range from 0.1 to 25% by weight and preferably from 1 to 10% by weight of the washcoat. The catalytic metals may be incorporated into or onto the surface of the monolith support including a coated or modified substrate in a manner generally recognized by the art. Incipient wetness from a salt solution of the catalytic metal is one example of a method for incorporating a metal catalytic component on the monolith support or modified (coated) monolith support.

The superficial liquid and gas velocities in the monolith channels are maintained to effect a desired conversion, e.g., 1% to 99% per pass. Typically, the superficial velocity through the monolith ranges between 0.1 to 2 meters per second with residence times of from 0.5 to 120 seconds.

Although not intending to be bound by theory, when a monolith support is used as a catalyst support, the morphology of the surface of the monolith support is important in order to (a) attach the active metal for hydrogenation for enhanced adhesion and (b) in the case of two immiscible liquid phases to permit selective adsorption of the reactant over the other immiscible phase, water, and the product for enhanced reaction rate.

In terms of a support for the catalytic metal, particularly a polymer network/carbon coating or carbon film carried on a substrate and thereby acting as a monolith support for the catalytic metal, eliminating micro porosity of the surface of the carbon coating or carbon film is advantageous for producing a monolith catalytic reactor having excellent activity and catalyst life. Small and medium size pores in the surface of the coating tend to lead to catalyst deactivation through pore plugging with high molecular weight co-products. Therefore, the carbon monolith support, a carbon coated substrate forming the monolith support or a polymer network/carbon coated substrate resulting in a monolith support should have a very low surface area for optimum activity, i.e., measured by adsorption of $N_2$ or Kr using the BET method of from approximately 0.1 to 15 $m^2$/gram of surface area.

To achieve the preferred polymer network/carbon coated monolith support having low surface area for use in forming the monolith catalytic reactor, polymer coating solutions are applied to the wall surface of the substrate and heated to a temperature below traditional carbonization temperatures. Examples of polymer forming solutions suited for producing polymer network/carbon coating include furfuryl alcohol solutions and solutions of furfuryl alcohol with other additives such as pyrrole and polyethylene glycol methyl ether. The furfuryl alcohol solutions may also be based upon prepolymers containing polymerized units of furfuryl alcohol. A preferred example is a furfuryl alcohol polymer solution derived from a furfuryl alcohol/pyrrole/polyethylene glycol methyl ether solution. An example of a copolymer is one based upon furfuryl alcohol and formaldehyde. Other examples include epoxy resins with amines;

epoxy resins with anhydrides; saturated polyester with glycerol or other multifunctional alcohols; oil-modified alkyd saturated polyesters, unsaturated polyesters; polyamides; polyimides; phenol/formaldehyde; urea/formaldehyde; melamine/formaldehyde and others. Preferred polymer network/carbon coatings are based upon commercially available oligomers and copolymers of furfuryl alcohol as the coating solution.

The polymer coating solution is applied to the monolith substrate as a thin film such that the interior dimensions of the cells in the monolith support are not altered significantly. It remains desired to have cell dimensions of the monolith support and thereby the monolith catalytic reactor within the 100 to 800 cpi range.

Carbonization of the polymer coating is effected at relatively low temperature in an effort to effect adhesion of the polymer network/carbon coating. Temperatures for carbonization in producing the unique polymer network/carbon coatings range from 250 to 350° C. vs. 550–900° C. commonly used for these polymer solutions in the prior art. Because of the lower carbonization temperatures used herein, network polymers having polar groups, particularly those based upon furfuryl alcohol, will retain some of their functionality and are more like the polymer than carbon. These functional groups also can be coupled through reaction chemistry to anchor homogeneous catalysts, homogeneous chiral catalysts or ligands to the polymeric surface.

Hydrogenation of organic compounds is effected at temperatures of 60–180° C. The hydrogenation pressure can be up to 1600 psig.

The following examples are intended to represent various embodiments of the invention and are not intended to restrict the scope thereof.

Preparation of Low Surface Area Polymer Network/Carbon Coated Monolith General Procedure Coating: A network polymer resin can be made from the polymerization of the appropriate monomers or oligomers. As an example furfuryl alcohol is polymerized with an acid at a controlled temperature to produce a coating solution. The acid can be inorganic (i.e. $HNO_3$, HCl, $H_2SO_4$) or organic (i.e. aromatic sulfonic). A dried monolith substrate or support is then soaked in the coating solution for 2–4 minutes, allowed to drip dry (removal of excess coating solution from the channels) and let dry. If it is observed that the monolith channels have become visually blocked by the polymer solution, the channels are blown clear with air. The coated monolith is further dried at 80° C. under a $N_2$ purge overnight.

Carbonization: The coated monolith substrate is mounted in a tube furnace and purged with $N_2$ while the heat is increased to 110° C. for 30 minutes. The tube is then continued to be heated until the tube surface temperature is 280° C. and held at 280° C. for 2 hours. The furnace is cooled to 260° C. and 5% $O_2$/He is introduced instead of the $N_2$. The tube containing the monolith is heated to 280° C. and held there for 40 minutes. The carrier gas is switched back to $N_2$ and the heat is turned off. The monolith is removed after reaching room temperature.

Metal Impregnation: The catalytically active metal is incorporated onto the coated monolith substrate by an incipient wetness technique, dried at 80° C. in an oven overnight with $N_2$ purge and then calcined at a tube surface temperature of 280° C. using $N_2$. The catalytic metal can also be pre-reduced before being used as a catalyst in a hydrogenation process. To be more specific, after the carbonization the amount of metal salt to dissolve or standard metal solution to dilute based on previously determined pore volume is calculated. In a typical example of metal impregnation, a 2" diameter 400 cpi cordierite monolith 2" in height substrate is placed in a glass beaker containing approximately 80 ml of active metal solution. Additional solution is added to cover the monolith support if necessary. The monolith substrate is soaked for approximately 30 minutes or until no bubbles are seen. The solution is poured from the container, the monolith is removed and excess solution from channels is cleared by a low flow of air. The monolith is set in the hood for approximately 1 hr., and periodically checked to see if channels remain cleared. If channels are not clear, blow through with low flow of air. The monolith is placed in an 80° C. oven with $N_2$ purge overnight. After removal of the monolith from the oven, let it cool in desiccator. The monolith is then heated in a tube furnace at a tube surface temperature of 280° C. using $N_2$ for 2 hours thereby forming a monolith catalytic reactor.

Preparation of Catalyst A—Low Surface Area Polymer Network/Carbon Coated Monolith Support Coating: Three hundred (300) ml of furfuryl alcohol, 150 ml of melted polyethylene glycol methyl ether (MW ~750) and 90 ml of pyrrole were added to a beaker. While stirring the three component mixture, the temperature was lowered to approximately 17° C. To this mixture are added small increments of 70% $HNO_3$ (20 ml total) while controlling the temperature at less than 20° C. After the addition of the acid, the mixture is stirred for 1 hr. while maintaining temperature at approximately 21–23° C. Place monolith substrate in a suitable container and pour sufficient polymer solution prepared above to completely cover the element. Let the monolith substrate soak until no bubbles are observed at the liquid surface. Remove the monolith from the polymer solution and let it drain briefly, then re-immerse in the polymer solution. Again remove the monolith from the polymer solution, let drain and blow down the channels to assure a uniform polymer coating with no blocked channels. Place the coated monolith in a 80° C. oven with a $N_2$ purge for overnight.

Carbonization/Activation: The coated monolith substrate is placed in a quartz tube which is mounted in a vertical tube furnace. The quartz tube is purged with $N_2$ and heated to a tube surface temperature of 110° C. at a rate of about 10° C. per minute. The temperature is held at 110° C. for 30 minutes. The temperature of the tube surface is increased to 280° C. at 10° per minute and held at 280° C. for 2 hrs. The tube surface is cooled to about 260° C. Then the $N_2$ is switched to 5% $O_2$ in an inert gas. The tube containing the monolith is heated to 280° C. and held at 280° C. for approximately 40 minutes. The 5% in an inert gas is switched back to $N_2$ and a $N_2$ purge is maintained while cooling to room temperature.

Metal Impregnation: Determine the water absorption and then calculate the metal concentration required to attain the desired metal loading. Place the carbonized/activated polymer coated monolith in a suitable container and pour the metal solution to cover the monolith completely. Let the monolith soak for about 30 minutes or until no bubbles are observed at the liquid surface. Remove the monolith from the container, drain and blow down the channels to remove any excess solution. Place monolith in a 80° C. oven with a $N_2$ purge for overnight.

Catalyst Activation: Place monolith support consisting of coated monolith substrate in the quartz tube which is mounted in a vertical tube furnace as described above under Carbonization/Activation. Purge the quartz tube with $N_2$ for about 10 minutes. Heat to a tube surface temperature of 110° C. at a rate of about 10° C. per minute. The temperature is held at 110° C. for 30 minutes. The temperature of the tube surface is increased to 280° at 10° C. per minute and held at 280° C. for 2 hrs. If desirable, introduce a reducing gas, such as 4% $H_2$ in $N_2$, and hold at 280° C. for 2 hrs. The tube is purged with $N_2$ and cooled to ambient temperature with $N_2$. At ambient temperature the monolith catalytic reactor is passivated after the reduction step in a flowing inert gas stream containing 5% $O_2$ for 30 minutes.

Hydrogenation Rate Determination In Monolith Screening Reactor

A 2-liter batch autoclave reactor was fitted with a dual-function impeller, oriented above a catalyst holder for the monolith catalytic reactor, capable of inducing gas and pumping the gas-liquid dispersion through the catalyst bed. For the reactions studied, the typical combined liquid volume of reagents was 1 liter. The autoclave reactor was equipped with a dip tube to transfer the liquid reaction solution to a recovery cylinder. The portion of the reaction solution which was removed, was diluted and an internal standard added. Gas chromatography was used to perform a quantitative product analysis to calculate selectivity and conversion.

The raw hydrogen pressure data was corrected for compressibility. A hydrogen uptake curve was obtained as a function of reaction time. This curve was used to calculate rate data at various stages of conversion.

Comparative Example 1

Hydrogenation of Nitrobenzene in Monolith Catalytic Reactor Reactor using a Cosolvent, Isopropanol A series of monolith hydrogenation catalytic reactors having varying organic coatings was used to effect the hydrogenation of nitrobenzene (NB). Hydrogenation was carried out at a concentration of 40 wt. % NB in isopropanol and the rate of hydrogenation was measured at 50% conversion. All of these monolithic hydrogenation catalysts were tested in one liquid phase. Isopropyl alcohol was added as a solvent in order to make miscible the two immiscible phases of nitrobenzene and water. Reaction conditions consisted of 120° C., 200 psig $H_2$ at a stirring rate of 1500 rpm.

The column in Table 1 marked initial rate is the second experiment run in the batch autoclave and the column marked final rate is the eighth experiment at the same set of conditions and using the same catalyst. The rate, at 50% conversion, is expressed in moles $H_2$ per $m^3$ catalyst per second. Selectively in mol % is determined at 100% conversion. The adsorption of $N_2$ or Kr using the BET method was used to measure total surface area and the units are in $m^2$/gram. All % Pd are wt. % and based on total monolith weight.

TABLE 1

Pd on Carbon Monolith Hydrogenation Catalytic Reactors in One Liquid Phase

| Catalyst | Layer | Comment | Rate[1] (initial) | Rate (final) | Sel. to Aniline | Surface Area ($m^2$/gm) |
|---|---|---|---|---|---|---|
| A | polymer network/carbon | 1.5% Pd/C/ cordierite[2] | 92 | 91 | 97 | <1 |
| B | polymer network/carbon | 3.1% Pd/C/ cordierite[3] | 61 | 74 | 97 | 12 |
| C | polymer network/carbon | 2% Pd/C/ cordierite[4,5] | 47 | 20 | 97 | <1 |
| D | carbon composite | 1.7% Pd on C[5] | 20 | 13 | 98 | 466 |
| E | Carbon composite | 4.6% Pd on C[4,5] | 36 | 23 | 93 | 372 |
| F | Polymer network/carbon | 2% Pd/C/ cordierite[4,6] | 87 | 46 | 99 | <1 |
| G (control) | no carbon | 2% Pd/ cordierite | 33 | 16 | 98 | <1 |

[1]Moles $H_2$ per $m^3$ catalyst per second
[2]Furfuryl alcohol network polymer coating, low temperature carbonization, metal deposition, calcination as in general procedure
[3]Same catalyst formulation as Catalyst A-Higher Pd loading-Carbonization temperature is 550° C.
[4]Metal deposition and calcination as in general procedure
[5]C, D and E are developmental monoliths from commercial vendors
[6]The coating was made from a phenolic resin (Varcum)

Table 1 shows a general inverse trend between initial hydrogenation rate and surface area of the monolith support whether a carbon composite or a polymer network/carbon layer independent of catalyst loading. Polymer network/carbon coated substrate surfaces having an adsorption of $N_2$ or Kr using the BET method of 12 or less $m^2$/gram provided high initial and final hydrogenation reaction rates. This is contrary to the teachings in the scientific literature that a high surface area catalyst is more catalytically active. Except for one carbon based monolith support from a commercial vendor, all monolith catalytic reactors based upon, either carbon or polymer network/carbon coated monolith substrates, were more active than the control Catalyst G based on a support which did not have any carbon or added layer. In addition, the organic coatings made from furfuryl alcohol or a phenolic resin both have a low surface area layer and high initial hydrogenation rates. But, the monolith support consisting of the furfuryl alcohol based coating layer on a monolith substrate used in Catalysts A and B did not show a drop in hydrogenation activity after 8 runs. Catalyst A which was based upon a monolith support comprised of a polymer network/carbon coating on a carbon substrate and carbonized at low temperature retained some functionality vis-à-vis Catalyst B which was based upon a polymer network/carbon coating carbonized at a high temperature.

Catalyst A had significantly higher initial and final hydrogenation rates and at a lower catalyst metal loading. Except for Catalyst E (carbon composite monolith) all catalysts gave aniline selectivity greater than approximately 97 mol %.

EXAMPLE 2

Evaluation of Monolith Catalytic Reactors for Nitrobenzene Hydrogenation without a Cosolvent— Two-Phase A series of monolith catalytic reactors based upon a monolith support having a polymer network/carbon coated on cordierite catalysts were tested using neat nitrobenzene as the reactant. Conditions were similar to Example 1 except that the reaction system comprised two liquid phases. These results are shown in Table 2.

TABLE 2

Pd on Carbon Monolith Hydrogenation Catalytic Reactors in Two Immiscible Phases

| Catalyst | Layer | Rate[1] (initial) | Sel to Aniline |
|---|---|---|---|
| A | polymer network/carbon | 42 | 99 |
| B | polymer network/carbon | 44 | 99 |
| F | polymer network/carbon | 33 | 99 |

[1]moles $H_2$ per $m^3$ catalyst per second; 120° C.; 200 psig; 1500 rpm

In each run the hydrogen uptake curve when re-plotted as the hydrogenation rate vs. time showed that the hydrogenation rate was nearly constant until toward the end of the reaction. The nearly constant hydrogenation rate was not expected since the co-product, water, is being formed during the reaction and two immiscible phases are present. As the concentration of the water increased it was expected that the hydrogenation rate should decrease, or become inconsistent. These results suggest that the hydrophobic surface layer may selectively adsorb the nitrobenzene to the catalytically active surface since these three monoliths had constant hydrogenation rates. Again in this example, Catalyst A which had half the metal loading to that of Catalyst B gave an equal hydrogenation rate.

EXAMPLE 3

Evaluation of Monolith Catalytic Reactors without a Cosolvent—Two-Phase Hydrogenation The procedure of Example 2 was repeated with the exception of the monolith catalytic reactor and the immiscible feed consisted initially of 34 wt. % nitrobenzene, 48 wt. % aniline and 18 wt. % water. The reaction temperature and pressure were 140° C. and 400 psig respectively.

The hydrogenation rates for Example 3 are shown in Table 3.

TABLE 3

Pd on Carbon Monolith Hydrogenation Catalytic Reactors in Two Immiscible Phases

| Catalyst | Layer | Rate[1] (initial) | Sel to Aniline |
|---|---|---|---|
| A | polymer network/carbon | 124 | 97 |
| D | carbon composite | 19 | 97 |
| E | carbon composite | 21 | 78 |
| G | cordierite/no carbon | 17 | 96 |

[1]moles $H_2$ per $m^3$ catalyst per second; 140° C.; 400 psig; 1500 rpm

The polymer network/carbon coated cordierite monolith support used in forming Catalyst A, and the carbon composite monolith supports used in forming Catalysts D and E all gave nearly constant hydrogenation rates in two immiscible phases when the hydrogen uptake curve was re-plotted as the hydrogenation rate vs. time. There was a marked drop in aniline selectivity with Catalyst E which had a very high surface area. Note the high reaction rate for Catalyst A even though there was a significant amount of water in the reaction product.

Comparative Example 4

Evaluation of Monolith Catalytic Reactors for Nitrobenzene Hydrogenation using a Cosolvent, Isopropanol The procedure of Example 1 was repeated with the exception of the monolith catalytic reactor employed in the hydrogenation. Catalyst J was made from a support based upon a carbon layer cordierite and the carbon layer was made by a modified carbonization procedure. The carbonization procedure consisted of 650° C. with a $N_2$ purge for 2 hours followed by 5% $O_2/N_2$ at 450° C. for 40 minutes. The surface area by $N_2$ BET of the resulting monolith support was 40–70 $m^2$ per gram.

Table 4 illustrates the effect of a high temperature carbonization procedure on the hydrogenation activity. Hydrogenation was carried out at a concentration of 40 wt. % NB in isopropanol. As the surface area of the monolith increases the hydrogenation activity decreases.

TABLE 4

Pd on Carbon Monolith Hydrogenation Catalytic Reactors in One Liquid Phase

| Catalyst | Layer | Rate (initial)[1] | Rate (final) | Sel. to Aniline[2] | Surface Area ($m^2$/gram) |
|---|---|---|---|---|---|
| A | polymer network/carbon | 92 | 91[3] | 97 | <1 |
| B | polymer network/carbon | 61 | 74[3] | 98 | 12 |
| J | carbon | 37 | 24[4] | 99 | 40–70 |

[1]Moles $H_2$ per $m^3$ catalyst per second
[2]Selectivity determined at final experiment
[3]Final rate is the eighth experiment at the same set of conditions
[4]Final rate is the seventh experiment at the same set of conditions The results show that the high temperature carbonization of the network polymer in forming Catalyst B using furfuryl as was used in forming Catalyst A resulted in producing a higher surface area catalyst and significantly lower hydrogenation rates.

EXAMPLE 5

Evaluation of Monolith Catalytic Reactors for Nitrobenzene Hydrogenation

The procedure in Example 1 was repeated and a comparison was made between one liquid phase and two liquid immiscible phases. The molar concentration of nitrobenzene in the one liquid phase and two liquid immiscible phase experiments was the same. Table 5 shows the rate of hydrogenation at 50% conversion for three catalysts with different carbon surface areas.

TABLE 5

Pd on Carbon Monolith Hydrogenation Catalytic Reactors

| Catalyst | Layer | Liquid Phases | Rate[1] | Sel. To Aniline | Surface Area (m²/gram) |
|---|---|---|---|---|---|
| A | polymer network/carbon | 1[2] | 91[4] | 97 | <1 |
|   |   | 2[3] | 46[4] | 99 |   |
| F | polymer network/carbon | 1[2] | 46[4] | 99 | <1 |
|   |   | 2[3] | 41[4] | 99 |   |
| J | polymer network/carbon | 1[2] | 24[5] | 99 | 40–70 |
|   |   | 2[3] | 21[5] | 99 |   |

[1]moles $H_2$ per $m^3$ catalyst per second; Pd/C/cordierite
[2]One phase: 2.97M NB (40 wt %) in isopropanol
[3]Two phases: 2.97M NB (34 wt %) in 48 wt % aniline and 18 wt % water
[4]120° C.; 200 psig; 1500 rpm
[5]140° C.; 200 psig; 1500 rpm The Catalysts, A and F, in general, have faster hydrogenation rates in either one phase or two phases when the total surface area is less than 40 m²/gram. Catalyst A showed a difference in reaction rate depending on whether the reaction medium was one phase or two phases. Surprisingly, on the other hand Catalyst F or Catalyst J had equal to or only slightly improved hydrogenation rates when going from two liquid phases to one liquid phase.

EXAMPLE 6

Evaluation of Monolith Catalytic Reactors for Nitrobenzene Hydrogenation

The procedure in Example 1 was repeated in order to compare the activity of the monolith catalytic reactor where the coating layer is made by the polymerizing of furfuryl alcohol or from a preformed co-polymer of furfuryl alcohol. The hydrogenation was carried out at a concentration of 40 wt % NB in isopropanol. Reactions conditions were 120° C., 200 psig $H_2$ at a stirring rate of 1500 rpm.

TABLE 6

Pd on Carbon Monolith Hydrogenation Catalytic Reactors in One Liquid Phase

| Catalyst | Layer | Comment | Rate[1] (initial) | Sel. To Aniline | Surface Area (m²/gm) |
|---|---|---|---|---|---|
| A | polymer network/carbon | 2% Pd/C/ cordierite[2] | 92 | 97 | <1 |
| K | polymer network/carbon | 2% Pd/C/ cordierite[3] | 53 | 99 | <1 |
| G (control) | no carbon | 2% Pd/ cordierite | 33 | 98 | <1 |

[1]Moles $H_2$ per $m^3$ catalyst per second
[2]Furfuryl alcohol polymer network coating, low temperature carbonization, metal deposition, calcination as in procedure
[3]Co-polymer of furfuryl alcohol-formaldehyde resin and phenol sulfonic acid catalyst with pyrrole and polyethylene glycol methyl ether, low temperature carbonization, metal deposition, calcination as in procedure Catalyst K is a polymer network/carbon coating layer made in accordance with the general procedure used in forming Catalyst A but from a coating solution consisting of furfuryl alcohol-formaldehyde resin, furfuryl alcohol, phenol sulfonic acid, pyrrole and polyethylene glycol methyl ether.

What is claimed is:

1. A monolith catalyst comprised of a monolith support and a catalytic metal wherein said monolith support is comprised of a substrate consisting of honeycomb of long narrow channels or cells and having from 100 to 800 cells per square inch, said substrate coated with a polymer network/carbon having a coating surface area of from 0.1 to 15 m²/gram as measured by adsorption of $N_2$ or Kr using the BET method.

2. The monolith catalyst of claim 1 wherein the polymer network/carbon coating is formed from a furfuryl alcohol containing polymer forming solution or a prepolymer containing polymerized units of furfuryl alcohol.

3. The monolith catalyst of claim 2 wherein the catalytic metal is applied to the surface of the polymer network/carbon coating.

4. The monolith catalyst of claim 3 wherein the catalytic metal deposited on the surface of the polymer network/carbon coating is a Group VIb, Group VIIb, or Group VIII or Group Ib metals.

5. The monolith catalyst of claim 4 wherein the catalytic metal is selected from the group consisting of rhodium, cobalt, Raney or sponge nickel, palladium, platinum, copper, ruthenium and rhenium.

* * * * *